United States Patent [19]

Reger et al.

[11] Patent Number: 5,108,419

[45] Date of Patent: Apr. 28, 1992

[54] ENDOVASCULAR FILTER AND METHOD FOR USE THEREOF

[75] Inventors: Vincent A. Reger, Portland; Thomas L. Kelly, West Linn, both of Oreg.; LeRoy E. Groshong, Vancouver, Wash.

[73] Assignee: EVI Corporation, Portland, Oreg.

[21] Appl. No.: 568,844

[22] Filed: Aug. 16, 1990

[51] Int. Cl.⁵ .................................................. A61M 25/00
[52] U.S. Cl. ................................... 606/200; 606/159
[58] Field of Search .................... 606/200, 198, 159; 128/899

[56] References Cited

U.S. PATENT DOCUMENTS

| | | | |
|---|---|---|---|
| 3,334,629 | 8/1967 | Cohn | 606/194 |
| 3,472,230 | 10/1966 | Fogarty | 128/328 |
| 3,540,431 | 11/1970 | Mobin-Uddin | 128/1 |
| 3,952,747 | 4/1976 | Kimmell, Jr. | 128/303 |
| 3,996,938 | 12/1976 | Clark, III | 128/348 |
| 4,425,908 | 1/1984 | Simon | 128/1 |
| 4,494,531 | 1/1985 | Gianturco | 128/1 |
| 4,619,246 | 10/1986 | Molgaard-Nielsen | 128/1 |
| 4,650,466 | 3/1987 | Luther | 604/95 |
| 4,669,464 | 6/1987 | Sulepov | 606/200 X |
| 4,688,553 | 8/1987 | Metals | 128/1 |
| 4,706,671 | 11/1987 | Weinrib | 128/348.1 |
| 4,723,549 | 2/1988 | Wholey et al. | 128/344 |
| 4,727,873 | 3/1988 | Mobin-Uddin | 128/303 |
| 4,745,919 | 5/1988 | Bundy et al. | 128/305 |
| 4,755,175 | 7/1988 | Nilsson | 604/268 |
| 4,790,812 | 12/1988 | Hawkings, Jr. et al. | 604/22 |
| 4,793,348 | 12/1988 | Palmaz | 128/325 |
| 4,832,055 | 5/1989 | Palestrant | 128/899 |
| 4,873,978 | 10/1989 | Ginsburg | 606/198 |
| 4,886,061 | 12/1989 | Fischell et al. | 128/305 |
| 4,921,484 | 5/1990 | Hillstead | 604/104 |
| 4,926,858 | 5/1990 | Gifford et al. | 606/159 |

Primary Examiner—Michael H. Thaler
Attorney, Agent, or Firm—Lynn G. Foster

[57] ABSTRACT

A filter useful in tubular organs of the human body, intended primarily for endovascular use during surgical procedures for removal of plaque and other treatment of stenoses in arteries, in order to entrap particles of plaque or other materials freed from the interior wall of an artery while permitting continued flow of blood through the artery during the procedure of treating the stenosis. Several filter elements are fastened in apart-spaced relationship with one another along a flexible elongate member and are large enough to require the entire flow of blood through the artery to pass through the filter elements. An open-mouthed tubular stocking of porous filter material encloses the filter elements and supports the periphery of each filter element. Successive filter elements, progressing in the direction of blood flow, pass only progressively smaller particles. In a preferred embodiment, the mouth of the stocking can be closed to retain particles of material within the filter as it is written from the artery after repair of a stenosis.

33 Claims, 7 Drawing Sheets

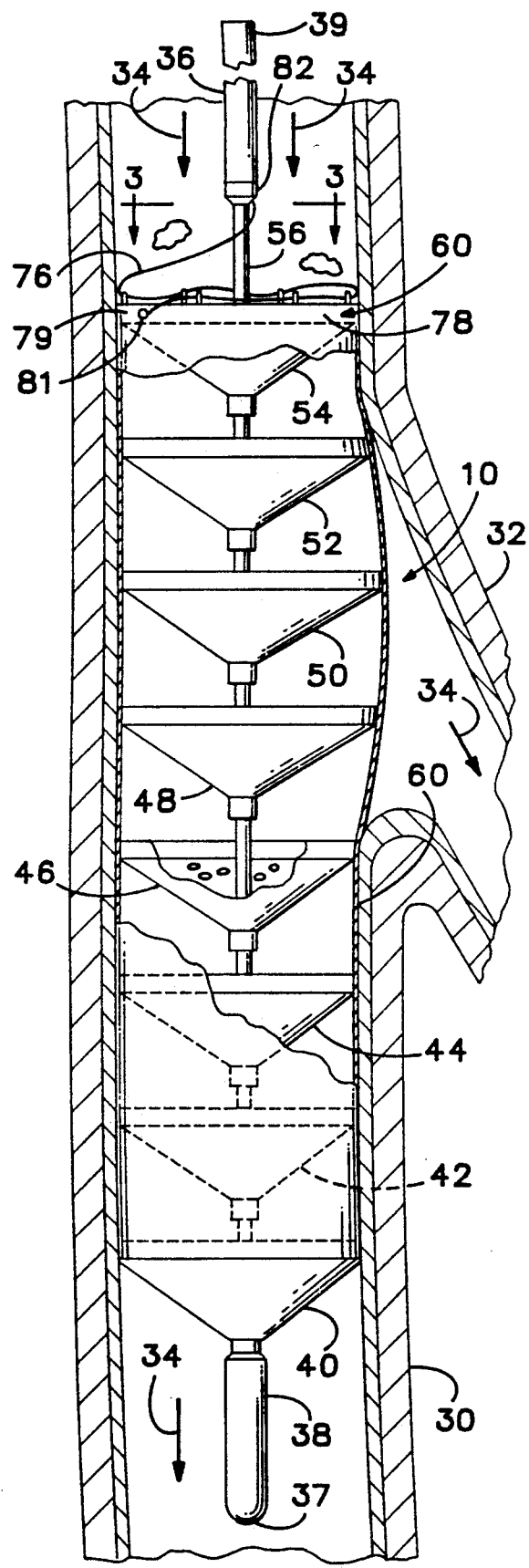
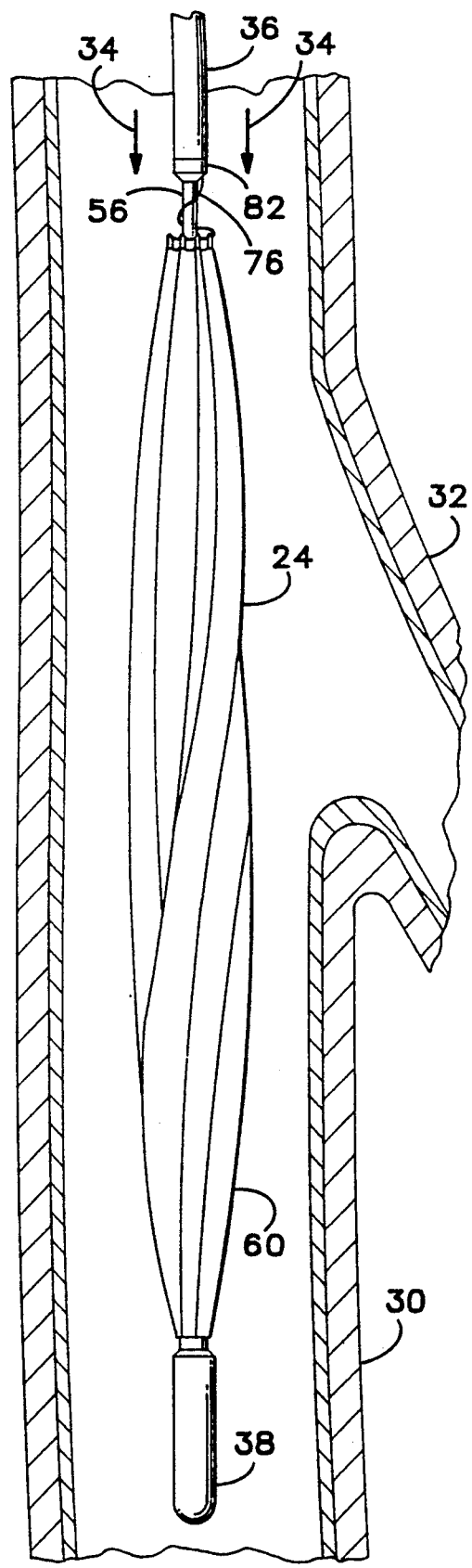
FIG. 2
FIG. 8

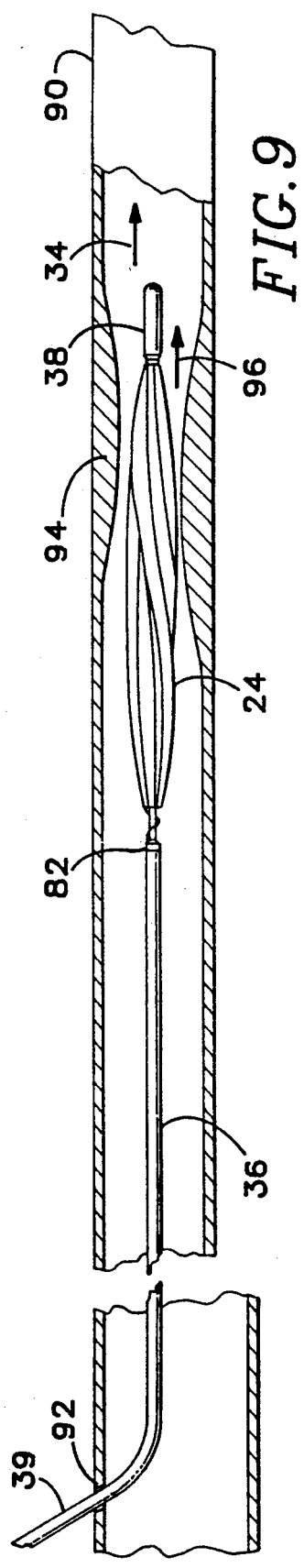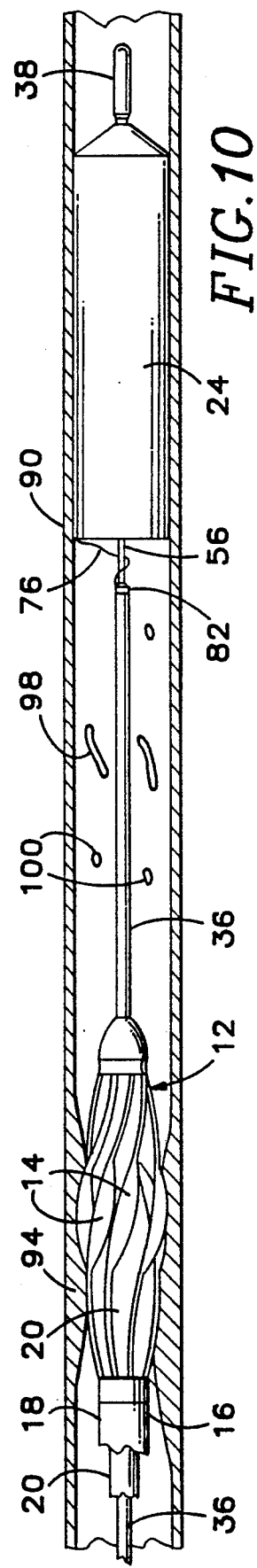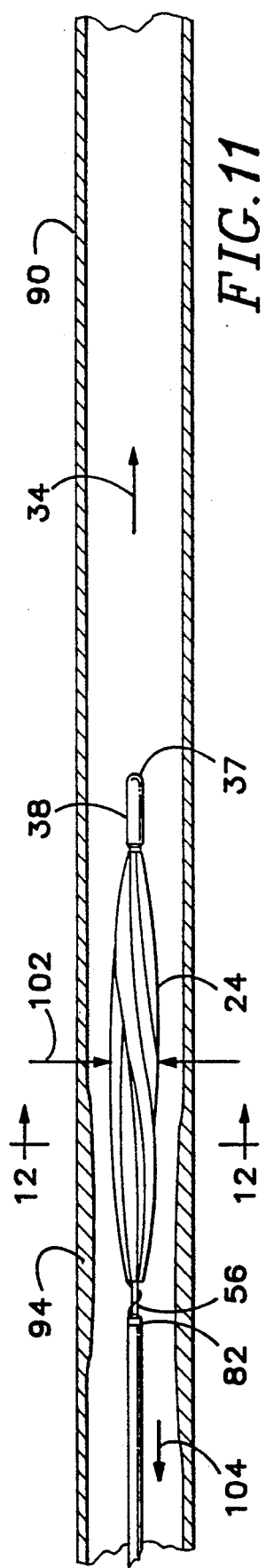

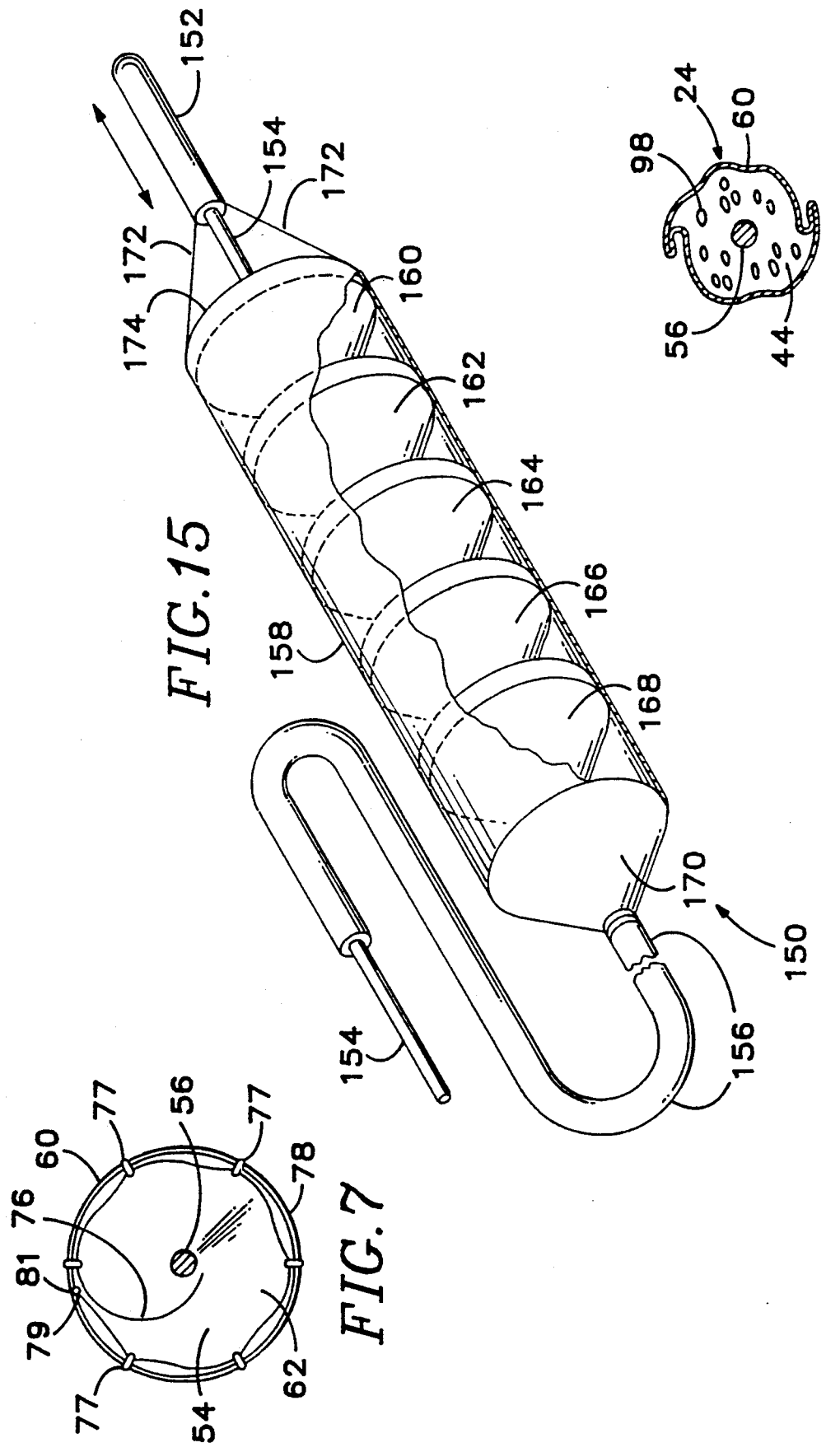

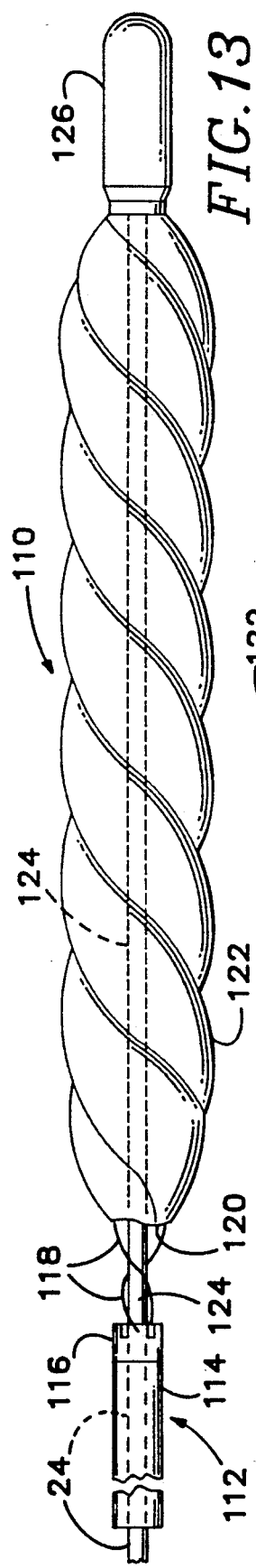

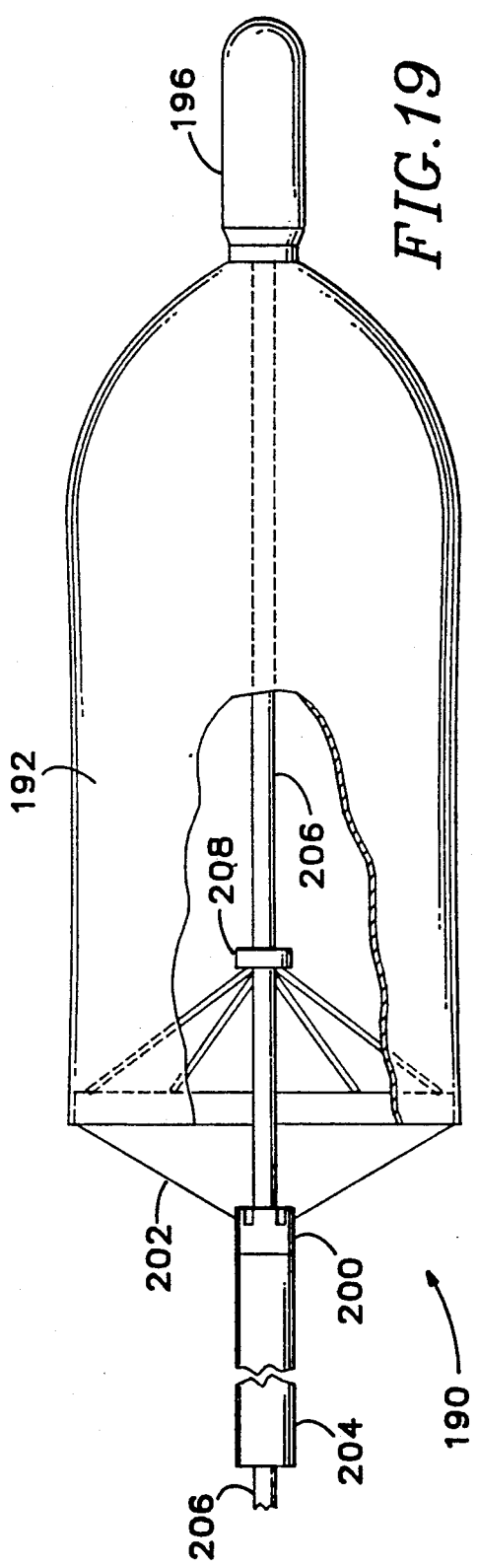
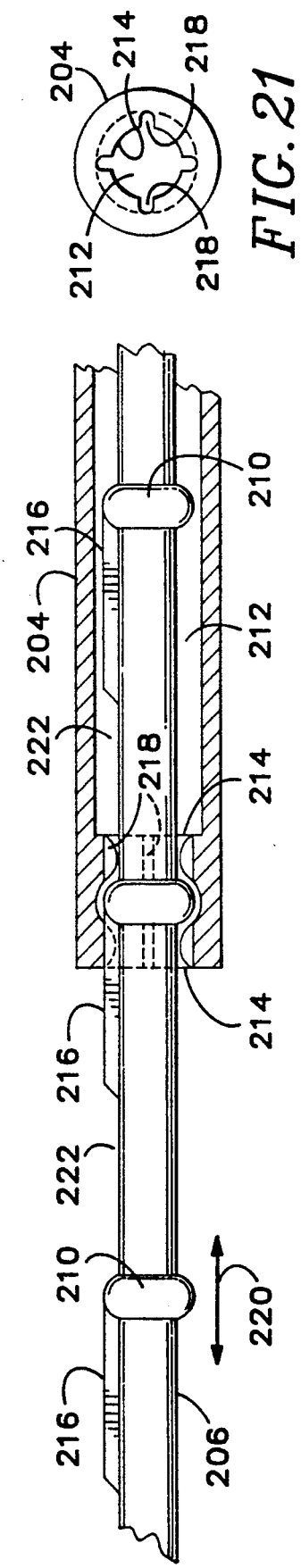

ENDOVASCULAR FILTER AND METHOD FOR USE THEREOF

BACKGROUND OF THE INVENTION

The present invention relates to filtration of fluid flow in tubular bodily organs, such as arterial and venous bloodstreams and the urinary tract, and particularly to a filter device for use during angioplasty and atherectomy procedures for relief of stenoses.

Occlusion of arteries by deposition of plaque or by thrombosis ultimately results in lack of sufficient blood flow to tissues served by the occluded artery, and eventually may result in necrosis. Patency of the lumen of an artery may be restored by different procedures including angioplasty and atherectomy, but these procedures may dislodge pieces of plaque or blood clots large enough to cause dangerous occlusion of smaller downstream vessels.

It is important not to have pieces of material such as plaque or blood clots significantly larger than blood cells moving freely in circulation in the blood vessels because of the danger of such particles lodging in a location which would interrupt the blood circulation to critical tissues such as heart muscle, brain tissue, etc.

Procedures in which foreign objects such as catheters are introduced into blood vessels may result in the formation of clots which might ultimately be released into the bloodstream. It is thus important in such procedures to prevent movement of dislodged blood clots or plaque and the like. and to capture and retrieve such pieces of material from within the blood vessel as a part of the completion of such procedures.

Various devices are known for the purpose of cutting or abrading plaque material from the interior lining of arteries. Their use has usually been accompanied by the need to prevent blood flow during the procedure, as by the use of a balloon-tipped catheter completely occluding an artery at a position downstream from a stenosis being treated by the procedure, in order to retain pieces of plaque freed from the arterial wall. However, balloon-tipped catheters do not always work satisfactorily to retrieve debris. They may squeeze pieces of plaque against an arterial wall, resulting in loose temporary adhesion and subsequent release into the blood stream. Additionally, use of a balloon-tipped catheter is necessarily of limited duration because of the resulting lack of blood circulation to tissues normally fed by the artery on which the procedure is being performed.

Various implantable filter devices are known for use in large veins, to trap blood clots and thus prevent them from being circulated into the heart, lungs and other bodily tissues where blood vessel blockage could be disabling or fatal. Such implantable blood filter devices, however, are not well adapted for use in connection with angioplasty or atherotomy, because the implantable devices are not easily removable. Additionally, such implantable devices are not likely to stop smaller pieces of material which might nevertheless be carried through the bloodstream to cause dangerous blockage of small arteries or capillaries. Such devices are disclosed, for example, in Mobin-Uddin U.S. Pat. Nos. 3,540,431 and 4,727,873, Kimmell, Jr. U.S. Pat. No. 3,952,747, Simon U.S. Pat. No. 4,425,908, Gianturco U.S. Pat. No. 4,494,531, Molgaard-Nielsen et al. U.S. Pat. No. 4,619,246, Metals U.S. Pat. No. 4,688,533, Palmaz U.S. Pat. No. 4,793,348, and Palestrant U.S. Pat. No. 4,832,055.

One filter-like device for use in connection with removal of plaque from within an artery is disclosed in Wholey et al., U.S. Pat. No. 4,723,549, but the process of withdrawing the device appears likely to release particles of plaque into the bloodstream, and the device appears likely to allow flow of unfiltered blood when it is located in a portion of a blood vessel with an irregularly or asymmetrically shaped lumen.

Clark, III, U.S. Pat. No. 3,996,938 discloses a cylindrical mesh tube with its opposite ends attached respectively to a tube and a central wire within the tube, so that relative movement of the wire and tube results in radial expansion and longitudinal contraction of the mesh material. The mesh material acts as a filter in order to remove a blood clot from within a blood vessel.

Luther U.S. Pat. No. 4,650,466 discloses a device somewhat similar to that shown in the Clark, III, patent but intended to be used for abrading plaque from an arterial wall and not to filter blood.

What is needed, then, is a device able to prevent downstream transport of materials significantly larger than blood cells, as well as a method for its use to permit the flow of blood to continue during a procedure, such as angioplasty or atherectomy to correct a stenotic condition in a blood vessel. Such a device preferably should be able to capture debris and permit retrieval of the debris without pieces of debris being released into the bloodstream, either during use or as a result of retrieval. Additionally, the device should be able to be configured small enough to pass a stenosis in an artery, yet be dependably expandable, to peripherally coapt completely with an irregular vessel wall, to fill the lumen of the artery at a location downstream from a stenosis, so that the entire bloodstream through the artery is filtered. Such a device also needs to be effective at a location where a branch diverts from the main stem of blood vessel at a location downstream of a stenosis being treated.

SUMMARY OF THE INVENTION

The present invention answers the aforementioned need for a device for filtering a flow of bodily fluid such as blood during certain procedures for the repair of stenoses in tubular organs such as blood vessels, and overcomes some of the aforementioned shortcomings of the previously known devices for filtering bloodstreams by providing an endovascular filter device and a method for its use. The filter device according to the present invention includes a filter assembly mounted on a flexible catheter or guide wire to permit it to be controllably placed into a desired position in a tubular organ such as an artery. Filter support members insure effective deployment of the filter in either fluid-flow or non-flow conditions, and give the filter the ability to expand toward and take the shape of an irregular surface of a tubular wall. The filter assembly provides single-stage or multi-stage filtration to minimize likelihood of the filter assembly becoming plugged by the material being filtered.

Several filter elements of the filter assembly are spaced apart from one another and mounted in series upon a slender support member, such as a catheter or guide wire, which can be located centrally within the lumen of the blood vessel whose flow of blood is to be filtered. Each filter element extends radially outwardly about the support member, and a tubular stocking of filter material in the form of a flexible thin sheet surrounds all of the filter elements and is interconnected with the periphery of each filter element. The stocking has an open mouth directed upstream so that blood flow, when present, helps to fill the filter and expand it to fill the entire lumen of the artery, ensuring that all blood must flow through each of the filter elements before proceeding further downstream through the artery.

Occasionally, initiation of filter removal must be preceded by initial withdrawal of the filter assembly still in an extended condition so that the vessel walls between the stenosis repair site and the location of the filter during the procedure can be "swept" clean of any debris that might have pooled or clung to that section.

Mechanisms are provided in the filter apparatus both to close the entrance to the filter and to refurl the filter elements and tubular stocking, to capture and realign the loose flaps and reduce the diameter of the filter stocking for safe withdrawal through access site sheaths.

In a preferred embodiment at least one drawstring is connected with the mouth of the stocking. In one embodiment of the device the drawstrings support the stocking, and through it support the filter elements to hold them generally transverse to the length of the artery. The drawstring or drawstrings are also useful to close the mouth of the stocking to retain trapped particles within the stocking during retrieval of the filter from its operative position within an artery.

In a preferred embodiment of the invention the filter elements and stocking are selectively controllable and movable with respect to the slender flexible support member, between a furled, reduced-diameter configuration and the larger-diameter operative configuration.

In a preferred embodiment of the invention the mouth of the stocking is selectively closeable to contain particles collected from the bloodstream during the course of a procedure to correct a stenosis, so that those particles are retained during removal of the filter device from its position in the artery.

In one embodiment of the invention several filter elements have different maximum pore sizes. The elements having larger pore sizes are located closer to the mouth of the stocking portion of the filter assembly, while the stocking itself and the filter elements further from the mouth of the stocking define pores of smaller size, capable of stopping any particles which are too large to proceed safely through a person's circulatory system, while permitting the passage of blood cells through the filter assembly.

In a preferred embodiment of the invention some or all of the filter elements are provided with flexible ribs, preferably extending radially away from the support member on which the filter elements are mounted, so as to urge the filter elements to expand to fill the lumen of blood vessel in which the filter is being used, while nevertheless permitting the stocking and filter elements to be contracted radially and furled for insertion and removal of the filter through the artery.

In one embodiment of the invention the more distally located filter elements may be extended radially to cause the stocking and proximal filter elements to expand radially outward to fill the lumen of a blood vessel.

In another embodiment of the invention a sleeve may be movably and controllably mounted on the guide wire and one or more articulated struts may be connected between the sleeve and the mouth of the stocking to open it selectively by moving the sleeve along the guide wire.

In another embodiment of the invention the mouth of the stocking may be forced open by slacking or pushing on a drawstring made of resilient material having a certain amount of stiffness, so that the drawstring urges the mouth of the stocking outward toward a greater radius.

It is therefore an important object of the present invention to provide a device for catching particles of arteriosclerotic plaque, blood clots, and other material carried in a bloodstream or through other conduits.

It is another object of the present invention to provide a filter device capable of containing materials which have been filtered from a stream of blood, so that the materials can be removed from a blood vessel with minimal danger of being released into the stream of blood during the procedure of removing the filter device from the blood vessels.

An important feature of the present invention is that it provides for filtration through filter media with successive stages having progressively smaller maximum pore sizes, in order to prevent early stoppage of the filter media.

A further important feature of the filter catheter of the present invention is the ability to "sweep" the walls of the vessel while still open to capture pooled or clinging debris where fluid flow is inadequate or non-existent.

Another important feature of the present invention is the provision of a drawstring closure to enclose pieces of material which have been filtered from the flow of blood.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

FIG. 2 is a sectional view of a portion of an artery in which the endovascular filter device shown in FIG. 1 is in use.

FIG. 5 is a detail view of the endovascular filter device shown in FIG. 1, at an enlarged scale, showing the relationship of the drawstring to the guide wire supporting the filter.

FIG. 6 is a sectional view of the portion of the endovascular filter device shown in FIG. 5, taken along line 6—6.

FIG. 7 is a sectional view, taken along line 7—7 of the filter device shown in FIG. 1.

FIG. 8 is a sectional view of the endovascular filter and portion of an artery shown in FIG. 2, with the filter assembly in its furled configuration following use and in preparation for withdrawal.

FIG. 9 is a partially cut-away view of a portion of an artery including a stenosis, with an endovascular filter according to the invention being passed through the stenosis in a furled configuration.

FIG. 10 is a sectional view of the portion of an artery and the endovascular filter shown in FIG. 9, with the filter in use, located downstream from the stenosis, while the catheter atherotome shown in FIG. 1 is being used to treat the stenosis.

FIG. 11 is a sectional view of the portion of an artery shown in FIGS. 9 and 10, showing the endovascular filter in a refurled configuration and being withdrawn through the repaired stenosis.

FIG. 12 is a sectional view of the filter assembly shown in FIG. 11, taken along line 12—12.

FIG. 13 is a view at an enlarged scale of a portion of an alternative embodiment of the filter device according to the invention.

FIG. 14 is a partially cut-away view of the filter device shown in FIG. 13, in its open, operative configuration, showing a structure for urging open the filter assembly.

FIG. 15 is a simplified, partially cut-away, view of a filter device according to the invention arranged for introduction into a tubular organ in a direction opposite the normal direction of fluid flow therein.

FIG. 16 is a view of an opener useful for urging outward the ribs of a filter spreader element.

FIG. 17 is a view of the opener shown in FIG. 16, together with a portion of a filter element spreader, with the spreader in a position for urging the filter element toward a reduced-diameter, or closed, configuration.

FIG. 18 is a fragmentary detail view of the opener and portion of a spreader element shown in FIG. 17, with the opener moved to a position in which it urges the rib of the spreader element toward an outwardly expanded, or open configuration.

FIG. 19 is a side elevational view of a filter device which is another embodiment of the present invention.

FIG. 20 is a partially cut-away side view of a proximal end portion of a two-stage guide wire including a locking mechanism and intended particularly for use in carrying a filter device according to the present invention.

FIG. 21 is a view taken in the direction indicated by the line 21—21 of FIG. 20 showing the angular position locking aspect of the mechanism shown in FIG. 20.

DETAILED DESCRIPTION OF THE INVENTION

Figure 1:
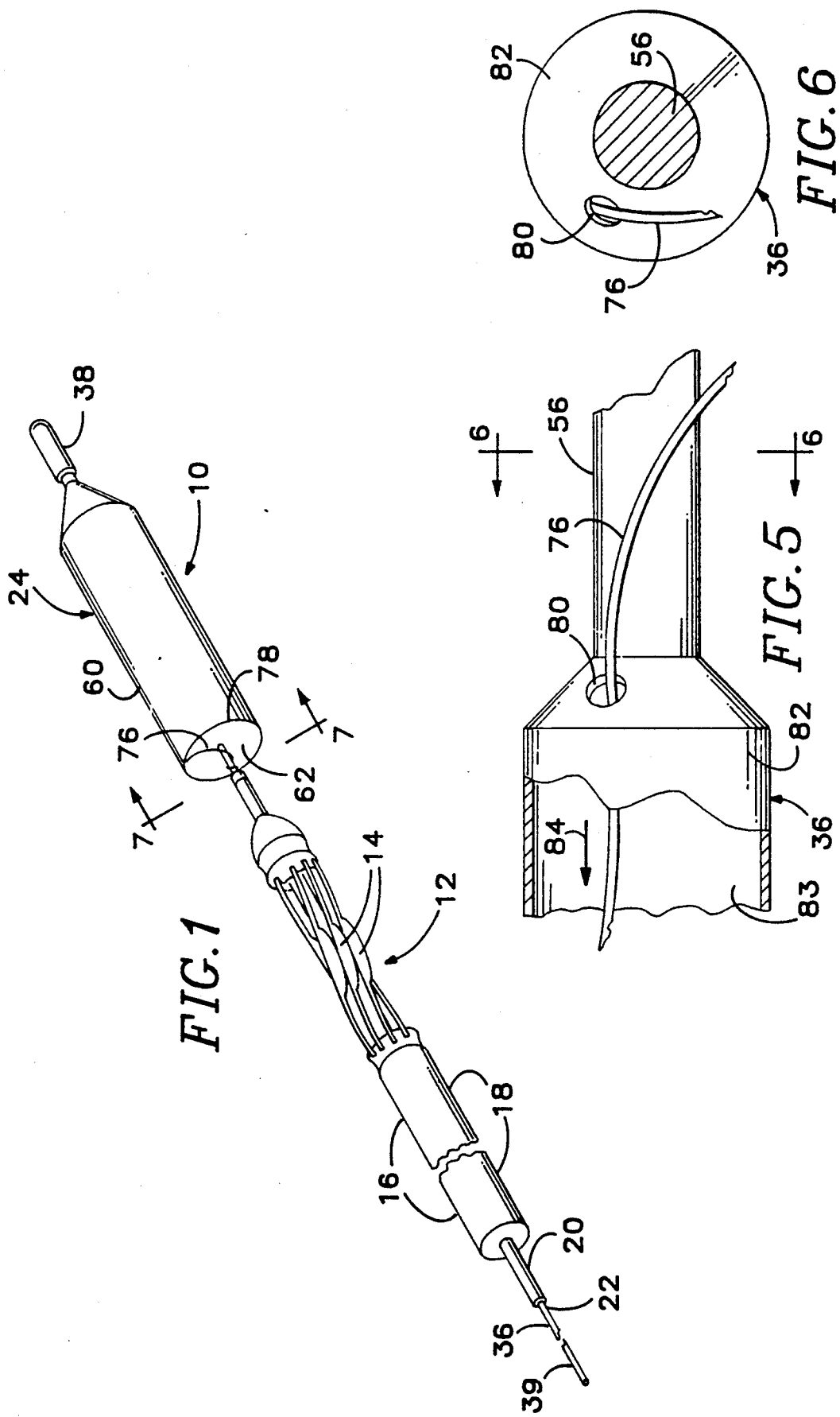
FIG. 1 is a perspective view of an endovascular filter device embodying the present invention, together with a catheter atherotome with which the filter device is useful.

Referring now to the drawings, in FIG. 1 a filter device 10 embodying the present invention is shown together with a catheter atherotome 12 which includes a plurality of sharp-edged cutter blades 14 carried adjustably on a catheter assembly 16 including an outer tube 18 and an inner tube 20. The catheter atherotome may be similar to that disclosed in pending U.S. patent application Ser. No. 07/395,500, filed Aug. 18, 1989 now abandoned. The inner tube 20 defines a lumen 22.

Referring also to FIG. 2, the filter device 10 includes a filter assembly 24 which is shown in an operative configuration in FIGS. 1 and 2. In FIG. 2, the filter assembly 24 is shown in an operative configuration and position within an artery 30 shown sectionally. A branch artery 32 extends from the artery 30 and is covered by the filter device 10. Arrows 34 indicate the direction of flow of blood through the arteries 30 and 32.

The filter assembly 24 is carried on an elongate, resiliently flexible, yet self-supporting stiff support member such as a hollow guide wire 36 including a distal end 37 and a proximal end 39. A suitable guide wire 36 may be similar to guide wires manufactured by Cook, Inc. of Bloomington, Ind., for use in leading catheters through tortuous passages in bodily organs. A tip portion 38 of the guide wire 36 is more easily flexible and can negotiate curves of small radius more easily than the remainder of the guide wire 36, as is well known in guide wires. Also, the guide wire 36 may instead be equipped with a J-tip (not shown) to facilitate selective negotiation of curves or branches of blood vessels into which the filter device 10 is to be introduced for use. The guide wire 36 extends through the lumen 22 of the inner tube 20 of the catheter atherotome 12, as shown in FIG. 1.

As shown best in FIG. 2 the filter device 10 exemplarily includes eight filter elements 40, 42, 44, 46, 48, 50, 52, and 54 of flexible material, although a different number of filter elements could be used instead without departing from the principles of the invention, depending on the size of the blood vessel in which the filter is to be used and on the size of particles of plaque and other debris to be captured by the filter. The filter elements are fixedly attached to a reduced diameter portion 56 of the elongate support member 36 and extend radially outwardly from the reduced diameter portion 56 in a generally circular, conical or arcuately curved configuration with each filter element disposed generally transverse to the reduced diameter portion 56. Each of the filter elements includes a respective peripheral portion 58 (FIG. 4), which is securely and tightly fastened, as by an adhesive or thermal weld, to the interior of a tubular stocking 60 of flexible filter material, which extends concentrically along the reduced diameter portion 56, defining a mouth 62 (FIG. 1), which opens generally toward the proximal end 39.

Figure 4:
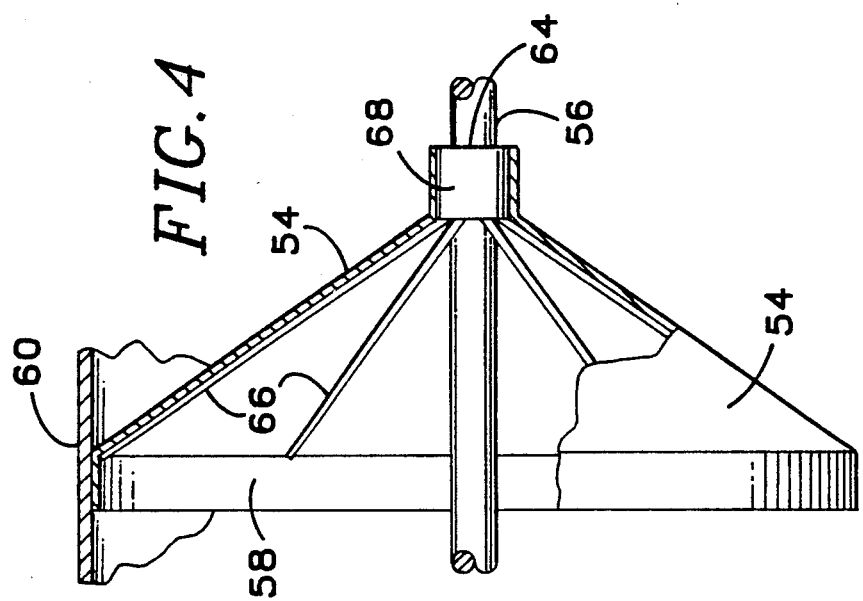
FIG. 4 is a partially cut-away view of the filter element shown in FIG. 3.
Figure 3:
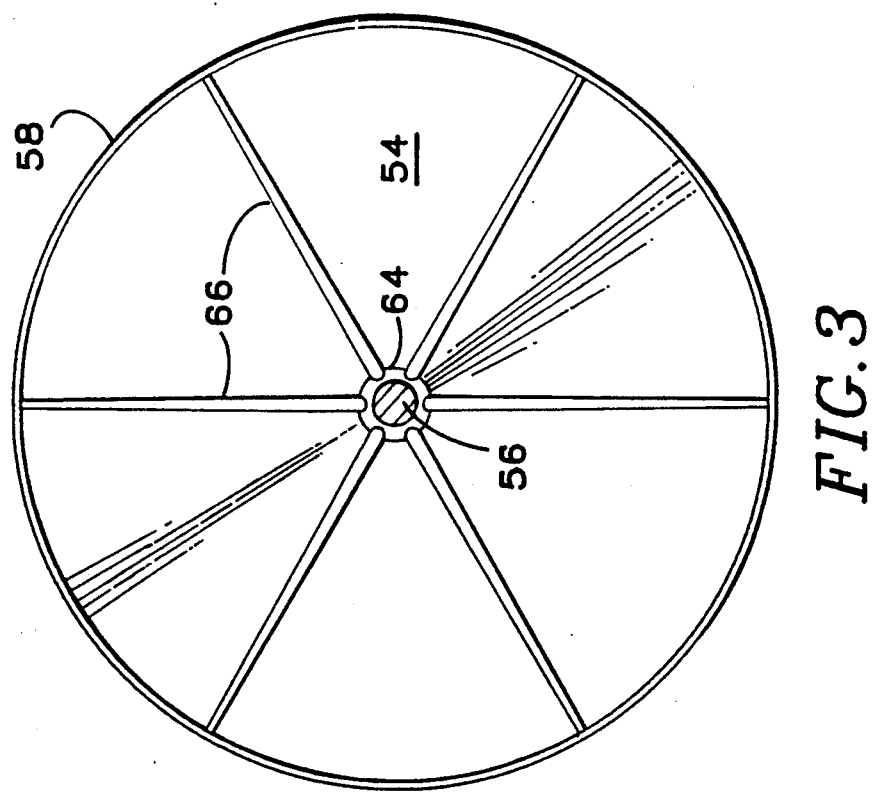
FIG. 3 is a view showing one filter element and supporting flexible ribs, taken along line 3—3 of FIG. 2.

Referring now also to FIGS. 3 and 4, the filter element 54, which is representative of all of the filter elements, is shown at an enlarged scale. Each of the several filter elements 42, 44, 46, 48, 50, 52, and 54 is preferably made of a porous membranous material. To the extent possible, each filter element has pores of substantially uniform size, but each filter element is of a filter material having a different pore size. The pore size of the filter element 40 is smallest, and each successively more proximally located one of the filter elements has larger pores, thus permitting passage of larger particles of material through the filter element 54 than through the filter element 52. The maximum size of particles able to pass through each of the successive filter elements thus is progressively smaller in each successive filter element in the direction in which blood must flow through the filter assembly 24, as is shown in Table I below.

TABLE I

| Filter Element (Reference Numeral) | 40 | 42 | 44 | 46 | 48 | 50 | 52 | 54 | 60 |
|---|---|---|---|---|---|---|---|---|---|
| Maximum opening size (microns) | 20 | 30 | 40 | 50 | 60 | 70 | 80 | 100 | 20 |

From Table I it may be seen that the pores of the filter element 40, which has the smallest pore size, are large enough to permit passage of particles which are somewhat larger than blood cells, but are too small to permit passage of particles likely to become lodged dangerously in blood vessels.

In order to prevent passage of dangerous particles from within the filter device 10 into, for example, a branch artery such as the branch 32, the stocking 60 is also formed of filter material having the same pore size as the filter element 40.

The filter elements 40, 42, 44, 46, 48, 50, 52, and 54, and the stocking 60 may be of material such as a porous layer of a polyester cloth, for example, manufactured to provide the desired pore sizes and with sufficient strength to resist the stresses of insertion of the filter assembly 24 (FIG. 1), into the artery 30 and subsequent withdrawal therefrom. At least one and preferably each filter element may be accompanied by a spreader element 64 which includes a plurality (six being shown) of radially extending ribs 66 and a central hub portion 68 attached to the reduced diameter portion 56 adjacent the central portion of the filter element 54, on the upstream (proximal) side of the filter element 54.

As will be understood more fully subsequently, it is important that the radial ribs 66 be flexible enough to permit the stocking 60 and filter elements 42–54 to be folded and furled into a reduced-diameter configuration as shown in FIG. 9, surrounding the reduced-diameter portion 56 of the elongate flexible member 36. At the same time the radial ribs 66 must be resilient enough to provide force to spread the respective filter elements across the lumen of the blood vessel at the appropriate time. Spreader elements 64 can be fabricated by molding appropriate plastic materials, such as polyethylene.

In order to close the mouth 62 of the stocking 60 when desired, a drawstring 76 is attached to the marginal portion 78 defining the mouth 62 of the stocking 60, as by loops 77, as shown in FIG. 7, for example. The drawstring 76 extends about the entire circumference of the mouth 62, with an end 79 of the drawstring being attached to the stocking 60 as at 81. Thence, the drawstring 76 continues radially inwardly, extending spirally about the reduced diameter portion 56 and through into an opening 80 defined in a collar fitting 82 defining the proximal end of the reduced diameter portion 56, and into a lumen 83 defined within the guide wire 36. As a result, when the drawstring 76 is pulled in the direction indicated by the arrow 84 shown in FIG. 5, the marginal portion 78 of the stocking 60 is drawn radially inwardly and spirally along the reduced diameter portion 56 toward the proximal end 39. This both reduces the opening provided by the mouth 62 and twists the entire stocking 60, as well as the respective filter elements, progressively about the reduced diameter portion 56, to achieve the configuration shown in FIG. 8, resembling an umbrella folded and furled about its handle.

The drawstring 76 extends through the lumen 83 defined in the guide wire 36 to the proximal end 39 and may selectively be moved longitudinally with respect to the outer portion of the guide wire 36 to control the distension or closing of the stocking 60 and filter elements 54, 52, etc. of the filter device 10.

In the embodiment of the filter device 10 shown in FIGS. 1–12 the drawstring 76 is of a resiliently flexible material having abrasion resistance and high tensile strength, for example wire, which has some inherent stiffness and tendency to become straight and thus open the mouth 62 when the drawstring 76 is pushed or when tension in it is relieved. This is intended to avoid the possibility of the marginal portion 78 of the stocking 60 folding inward against the reduced diameter portion 56 of the guide wire and closing off the mouth 62 or diverting the flow of blood around, rather than through, the filter assembly 24. Instead, the resilient drawstring 76 is intended to present the mouth 62 in an open configuration to completely fill the lumen of the artery 30 and allow the stocking 60 and the filter elements to be filled with blood.

However, in order to accomplish purse-like closing of the mouth 62 when appropriate, the drawstring 76 preferably extends slidably through the loops 77 located at intervals around the circumference of the mouth 62, as shown in some detail in FIG. 7. Thus, once the filter elements 54, 52, etc have entrapped particles of plaque or clots of blood, removing them from the flow of blood in the artery, the drawstring 76 is useful to close the mouth 62 tightly enough to capture and contain particles of plaque within the stocking 60 and between of the filter elements 40, 42, 44, etc.

This may be of particular importance in connection with atherectomy of coronary arteries where accessinto the coronary artery is obtained through the aorta, resulting in the filter device 10 later being withdrawn through the aorta in the direction of the flow of blood. In this situation, unless the mouth 62 is closed, the flow of blood within the aorta could force particles to be discharged from within the stocking 60 of the filter assembly 24. A more appropriate way to arrange the filter elements in an artery or vein where the flow (of blood) is reversed during the cutting procedure and/or withdrawal, is to orient the filter elements in the opposite direction, i.e., attaching the filter elements to the guide wires 36 and making the reduced diameter portion 56 a movable core, as shown in simplified form in FIG. 15 and described below.

Referring next to FIGS. 9, 10 and 11, the filter device 10 of the invention is used by inserting the distal end 37 into an artery such as the artery 90 through an opening 92 formed for the purpose, preferably percutaneously. The stocking 60 and filter elements 40, 42 etc. are furled tightly to the configuration shown in FIG. 9, so that the filter assembly 24 has a reduced diameter, and the guide wire 36 is utilized to push the filter assembly 24 through the artery 90 to the location of a stenosis 94 where an atherectomy procedure is to be performed. Led by the flexible tip 38, the filter assembly 24 is pushed through the stenosis 94 as indicated by the arrow 96 in FIG. 9, to a location a distance downstream from the stenosis 94, as shown in FIG. 10. The location of the filter assembly 24 at any particular time may be monitored by conventional means which need not be described here.

When the filter assembly 24 has been placed sufficiently far beyond the stenosis 94, the stocking 60 and filter elements 42, 44, etc. are deployed to fill the lumen of the artery 90 by relieving the tension in the drawstring 76, permitting it to move distally with respect to the guide wire 36. The mouth 62 is then opened as a result of the resiliency of the drawstring 76 as it slides through the loops 77, located along the marginal portion 78, attempting to increase the radius of curvature of the drawstring 76. Additionally, in a preferred embodiment of the filter assembly the resilient outwardly urgent bias of the radial ribs 66 of the spreader elements 64 helps to open each filter element 40, 42, etc., having an associated spreader element 64. Once the mouth 62 has opened appreciably the flow of blood into the interior of the stocking 60 may also aid in opening the filter assembly 24 into position to prevent material from flowing downstream beyond the filter assembly 24 except for having first passed through each of the filter elements.

Once the filter device 10 has been deployed to the condition shown in FIGS. 2 and 11, the proximal end 39 is threaded through the catheter atherotome 12 so that the atherotome can be inserted into the stenosis 94 guided by the elongate flexible guide wire 36 which forms a portion of the filter device 10. Upon utilization of the catheter atherotome 12, pieces of plaque 98 and 100 removed from the interior wall of the artery 90 will be carried along with the flow of blood in the direction of the arrow 34 into the interior of the filter assembly 24. Larger pieces of plaque, such as the pieces 98, will be entrapped in the filter elements having larger pores, such as the filter elements 54 or 52. Smaller particles such as the particles 100 are able to pass through the openings defined by the elements 54 and 52, but are later trapped by subsequent filter elements such as the filter element 46 or 44. The blood cells, being yet smaller, are able to pass through the entire filter assembly 24, including the stocking 60. Once the catheter atherotome 12 has satisfactorily enlarged the lumen of the artery 90 in the location of the stenosis 94 it is withdrawn along the guide wire 36 of the filter device 10 while the filter device 10 remains deployed as shown in FIGS. 2 and 10.

It will be recognized that it may be necessary to remove and reinsert the atherotome 12 one or more times before the stenosis 94 has been satisfactorily corrected, and so the filter device 10 is kept in place for that eventuality. Once the catheter atherotome 12 has been removed finally from the artery 90, so that there no longer is a likelihood of a blood clot or a piece of plaque being introduced into the bloodstream in the artery 90, the drawstring 76 is tightened, closing the mouth 62 of the stocking 60 and tending to furl the stocking 60 and the several filter elements 40, 42, 44, 46, 48, 50, 52, and 54, to reduce the diameter 102 of the filter assembly 24 to be somewhat smaller than the diameter of the lumen of the artery 90 or 30, as shown in FIGS. 8 and 11. This configuration, with a reduced diameter and with the mouth 62 held closed by the drawstrings 76, retains the pieces of material such as the pieces 98 and 100 of plaque which had been cut free from the interior of the arterial wall, while the filter assembly 24 is then removed as indicated by the arrow 104 in FIG. 11. Because the lumen of the artery 90 has been enlarged within the stenosis 94, the filter assembly 24, even with a somewhat greater diameter than that of its original furled configuration as shown in FIG. 9, can pass outward through the artery 90 to be removed through the opening 92 by which it was introduced into the artery 90.

At times during a procedure including the use of the filter device 10, the flow of blood through the artery being treated may be monitored, as by the use of a stethoscope, by blood pressure measurements, or other non-invasive techniques appropriate to the particular artery concerned.

Although it is preferred to treat the filter device 10 or the patient, or both, with an appropriate chemical compound such as heparin or streptokinase, to prevent undesired clotting of blood within the filter device 10, it will be recognized that clotting may occur in the filter device 10, and that it may be necessary to withdraw the catheter atherotome 12 and subsequently the filter device 10, in response to observed loss of blood flow downstream of the filter device 10 subsequent to the beginning of an atherectomy procedure. Ordinarily, however, it should be possible to observe the increase in flow of blood to tissue downstream of the filter 10 as use of the catheter atherotome improves the patency of the artery 90.

Referring to FIGS. 13 and 14, an alternative embodiment of the invention includes a filter assembly 110 associated with a guide wire 112 including an outer tube 114 with an end fitting 116, with a plurality (such as 6, for example) of flexible tension supports 118 extending from the end fitting 116 to a mouth 120 of a stocking 122 otherwise similar to the stocking 60. A core, or center wire member 124 whose diameter is smaller than that of the outer tube 114 supports several filter elements as in the filter assembly 24 shown in FIGS. 1-4, and a guide wire tip 126 extends beyond the distal end of the stocking 122. The tension supports 118 are connected both to the end fitting and to the mouth 116 of the stocking 122.

Referring now particularly to FIG. 14, the filter assembly 110 includes several, for example 6, filter elements 132, 134, 136, 138, 140, and 142, which are substantially similar to the filter elements 42, 44, etc. of the filter device 10 described hereinabove. Each of the filter elements 132, 134, etc., is similar in construction to the filter element 54, shown in FIGS. 3 and 4, and includes associated therewith a spreader element 144 equivalent to the spreader element 64 and including several radially extending ribs 146 which are resiliently flexible and are resiliently biased to force the respective filter elements outwardly toward the configuration shown in FIG. 14 when tension in the tension supporting members 118 is relaxed as a result of the relative movement of the center wire 124 approximately with respect to the outer tube 114, exposing the mouth 120 of the stocking 122 to the flow of blood through the blood vessel in order to trap particles of plaque, clotted blood, and the like which may be freed from the interior wall of the blood vessel as a result of the procedure being performed.

Once the filter assembly 110 has been placed in a blood vessel so that the filter stocking 122 is located downstream of a stenosis which is to be treated, as by use of a catheter atherotome, the center wire 124 is withdrawn proximally with respect to the outer tube 114 as indicated by the arrow 130, and is also rotated with respect to the outer tube 114, to relax the tension supports 118, as shown in FIG. 14.

Upon completion of the procedure and after removal of a catheter atherotome or other device used within a blood vessel upstream from the filter apparatus 110, the filter apparatus 110 can be prepared for removal by again moving the center wire 124 distally as indicated by the arrow 128 in FIG. 13, while preferably also rotating the center wire 128 with respect to the outer tube 114 to twist the stocking 122 and the flexible tension support members 118 into a helical, furled configuration resulting in a minimum diameter of the furled stocking 122, together with materials trapped within the filter device 110 during its withdrawal from the blood vessel where it has been used.

With the center wire 124 extending distally relative to the outer tube 114 as indicated by the arrow 128 in FIG. 13, the filter stocking 122 is held inward alongside the center wire 124. Preferably, the center wire 124 is also rotated with respect to the outer tube 114, so that the flexible tension supports 118 pull the stocking 122 into a helical, furled configuration fitting tightly about the center Wire 124, as shown in FIG. 13, to provide a slender configuration of the filter assembly 110 to aid in insertion through a blood vessel.

As shown in FIG. 15, a suitable filter device 150 according to the invention may also be made for insertion into a vessel such as an artery from a location downstream from a location where a procedure to be performed might result in dislodgment of particles of material which should not be permitted to escape into the flow of blood and potentially be carried to locations where the particles might harmfully obstruct smaller branches of the vessel. The filter device 150 as shown in FIG. 15, includes a flexible tip 152 on a core or center wire 154 which is movable relative to an outer sheath member 156 to which is attached a filter material stocking 158 similar to the stockings 60 and 122. Also attached to the outer sheath 156, within the stocking 158, are a plurality of filter elements 160, 162, 164, 166, and 168 similar to the filter elements 40, 42, etc. The filter elements define pore sizes permitting only progressively smaller particles to pass through successive ones of the filter elements in the direction from the distal end of the filter catheter device, the end closest to the flexible tip 152 of the center wire or core 154, toward the closed end 170 of the stocking 158, which is attached to the outer sheath 156. At least one drawstring, or support member 172, is attached to the open end of the stocking 158, near its mouth 174, and extends to the movable center wire 154 portion of the filter device 150, so that by extending and rotating the center wire 154 relative to the outer sheath 156 the mouth 174 of the stocking 158 may be drawn closed and the stocking 158 may be twistingly furled about the center core wire 154 to reduce the diameter of the filter and entrap and hold any particles which have been separated from a flow of blood or other fluid through the vessel in which the filter is used.

FIG. 16 shows an opener 180 useful for forcing open the mouth of a filter device, such as the filter assembly 110 shown in FIG. 14, which incorporates spreader elements similar to the spreader element 64 shown in FIGS. 3 and 4, but whose ribs are biased resiliently inwardly, tending to carry the filter elements supported by such a spreader element into a closed configuration such as the configuration of the filter assembly 110 as shown in FIG. 13. The opener 180 defines angled notches 182 equal in number to the number of radial ribs 184 (see FIGS. 17, 18), of the particular spreader element 186, allowing each rib 184 to rest close to a central core portion of the filter assembly when it is intended for the filter assembly to be in a closed configuration. When it is desired to open the filter assembly to occupy the lumen of a blood vessel, the opener 180 is moved toward the spreader element 186, as to the position shown in FIG. 18, in which the respective ribs 184 are urged outwardly by the opener 180 as a result of relative movement of the inner core member and the opener 180. This can be accomplished, for example, if the opener 180 is located in the position of the end fitting 116 of the filter assembly 110, in order to open a mouth portion of a filter stocking such as the filter stocking 122.

As may be seen in FIG. 19, a filter assembly 190 which is another embodiment of the invention includes a tubular stocking 192 having a closed distal end 194 attached to a flexible tip 196 of a two stage guide wire, but is without the additional filter elements used in the filter assembly as shown in FIGS. 2 and 14. An openable and closeable mouth 198 is attached to an end fitting 200 by tension-bearing closure members such as drawstrings 202 and is attached to the outer member 204 of the guide wire, whose smaller-diameter inner member 206 extends longitudinally through the interior of the stocking 192 to the guide wire tip 196. Preferably, there is a spreader element 208 similar to the spreader element 186, and the end fitting 200 includes the features of the opener 180 described hereinabove.

Referring now also to FIGS. 20 and 21, the proximal end portion of the guide wire of a filter assembly such as the filter assembly 190 may include a multi-position detent combination. In such a detent combination, the inner, or core portion 206 of the two-stage guide wire carries thereon a suitable number of radially outwardly extending annular detent collars 210 at predetermined positions along the length of the core member 206 at the proximal end of the guide wire.

The outer member 204 of the guide wire defines a lumen 212 whose size is sufficient to receive the detent collars slidably therein. A pair of inwardly protruding resilient locking rings 214 are located within the lumen 212, close enough to each other to receive and snugly hold one of the detent collars 210 between the pair of locking rings 214.

A fin or rib 216 extends along a portion of the core 206 extending proximally from each of the detent collars 210 for a short distance, and as may be seen with reference to FIG. 21, grooves 218 extend longitudinally through the locking rings 214 at a plurality of angularly separated locations about the locking rings 214. The grooves 218 permit sliding passage of the ribs 216 as the core member 206 is moved longitudinally within the outer member 204 as indicated by the arrow 220, with the core 206 in the proper angular alignment. Enough space is provided as at 222, between one of the ribs 216 and the next one of the locking rings 214, in a proximal direction along the core 206, to permit the core 206 to be rotated within the outer member 204 when all of the detent collars 210 are disengaged from a locking position between the pair of locking rings 214.

Thus the detent mechanism described above and shown in FIGS. 20 and 21 may be used to hold the associated filter assembly at the opposite end of the guide wire in a suitably open or closed position, depending on which of the detent collars 210 is held between the locking rings 214, and to prevent or cause twisting of the filter stocking of the filter assembly to furl or deploy the filter stocking, depending upon which of the angularly separated grooves 218 is used to retain the respective rib 216 associated with a particular one of the detent collars 210.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. An endovascular filter device, comprising:
   (a) a slender flexible elongate support member having a proximal end and a distal end adapted for insertion into and along the interior of a blood vessel; and
   (b) a filter assembly including:
      (i) plurality of flexible filter elements attached to a portion of said elongate member and spaced apart from one another therealong adjacent said distal end;

(ii) a flexible tubular porous stocking surrounding said filter elements and interconnected with each of them, said stocking having a mouth directed generally toward said proximal end of said elongate member; and (iii) means for supporting stocking with said mouth open to receive a flow of blood and with said filter elements in a flow-receiving and filtering position within said blood vessel.

2. The device of claim 1, including means associated with said stocking for selectively closing said mouth.

3. The filter device of claim 1 wherein each of said filter elements extends radially about said elongate support member and is attached thereto so as not to be movable longitudinally therealong, each of said filter elements having a periphery and said periphery of each of said filter elements being tightly interconnected with said stocking.

4. The device of claim 1 wherein said filter elements are each of flexible filter material preventing passage of particles larger than a predetermined maximum size, the maximum size of particles able to pass through respective ones of said filter elements located closer to said distal end of said flexible elongate member being smaller than the maximum size of particles able to pass through respective ones of said filter elements located further from said distal end of said flexible elongate member.

5. The device of claim 1 wherein said stocking is of a filter medium substantially preventing passage of particles which are larger than a predetermined size.

6. The device of claim 1 wherein said means for selectively closing said mouth includes a drawstring attached to said stocking and extending along said elongate flexible support member away from said distal end thereof.

7. The device of claim 1 wherein said elongate flexible support member includes a proximal portion which defines a lumen having an opening thereinto, located between said mouth of said stocking and said proximal portion, wherein said drawstring extends spirally along said flexible support member from said mouth of said stocking to said opening, so as selectively to draw said stocking into a furled configuration.

8. The device of claim 1 including a plurality of drawstrings arranged for coordinated application of tension thereto for drawing said stocking and said filter elements into a furled configuration.

9. The device of claim 1 wherein said elongate flexible support member is a guide wire and includes a flexible tip portion extending distally beyond all of said filter elements.

10. The device of claim 9 wherein said guide wire has a reduced diameter portion to which said filter elements are attached, said tip portion being larger in diameter than reduced diameter portion.

11. The device of claim 1 wherein at least one of said plurality of filter elements is generally conical.

12. The device of claim 1 including a set of flexible resilient ribs extending radially from said flexible elongate support member adjacent one of said filter elements so as to urge said filter element toward a radially extended configuration.

13. The device of claim 12 wherein said elongate support member includes first and second parts, and at least one tension support extending between and being interconnected with both the mouth of said stocking and said first part of said elongate support member, and said stocking having a distal end attached to said second part of said elongate support member, said second part being movable, between a first position, in which said tension support is sufficiently slackened to allow said resilient ribs to move a respective one of said filter elements toward said radially extending configuration, and a second position, in which said stocking and said tension support are in tension overcoming said resilient ribs and drawing said filter element radially inward toward said elongate support member.

14. The device of claim 13 wherein said first part of said elongate support member is a catheter defining a lumen and said second part thereof is a core longitudinally and rotatably movable within said lumen between said first and second positions.

15. A method of relieving a stenosis in an artery, comprising:

(a) providing an endovascular filter device including a plurality of flexible filter elements attached to an elongate flexible guide wire and surrounded by a tubular stocking of flexible filter medium attached to said filter elements;

(b) forming an opening in an artery in a location proximal of a stenosis and inserting said guide wire into said artery through said opening, with said filter elements and said stocking in a furled configuration;

(c) extending said filter device into said artery until said filter elements and stocking have passed through and a predetermined distance beyond a stenotic portion of said artery;

(d) thereafter unfurling said stocking and filter elements so as to deploy said filter elements across the interior of said artery;

(e) thereafter enlarging the lumen of said artery by freeing pieces of material from the stenotic portion of said artery; and (f) entrapping said pieces of material thus freed from said stenotic portion within said stocking.

16. The method of claim 15, including the further steps of closing said stocking so as to retain said pieces of material within said stocking, and withdrawing said filter device from said artery with said pieces of material retained within stocking.

17. The method of claim 16, said tubular stocking having a diameter, including the step of reducing the diameter of said stocking to a reduced diameter by twisting said stocking about said guide wire prior to removing said filter device from said artery.

18. The method of claim 16 wherein said stocking includes a mouth, the method including drawing said mouth tightly closed as part of said step of closing said stocking.

19. The method of claim 15, including the further step of monitoring blood pressure downstream of said filter device while freeing said material from said stenotic portion of said artery, and withdrawing said filter device from within said artery in response to a predetermined decrease in blood pressure downstream.

20. The method of claim 15 including the step of moving said filter device along said artery toward the location of said stenosis in a deployed configuration after performing said step of freeing pieces of material, so as to sweep said pieces of material away from the interior surface of said artery.

21. An endovascular filter device, comprising:

(a) a slender flexible elongate support member having a proximal end and a distal end adapted for insertion into and along the interior of a blood vessel; and (b) a filter assembly including:

(i) plurality of flexible filter elements attached to a portion of said elongate member and spaced apart from one another therealong adjacent said distal end;

(ii) a flexible tubular porous stocking surrounding said filter elements and interconnected with each of them, said stocking having a mouth directed generally toward said distal end of said elongate member; and (iii) means for supporting said tubular stocking with said mouth open to receive a flow of blood and with said filter elements in a flow-receiving and filtering position within said blood vessel.

22. The device of claim 21, including means associated with said stocking for selectively closing said mouth.

23. The filter device of claim 21 wherein each of said filter elements extends radially about said elongate support member and is attached thereto so as not to be movable longitudinally therealong, each of said filter elements having a periphery and said periphery of each of said filter elements being tightly interconnected with said stocking.

24. The device of claim 21 wherein said filter elements are each of flexible filter material preventing passage of particles larger than a predetermined maximum size, the maximum size of particles able to pass through respective ones of said filter elements located closer to said distal end of said flexible elongate member being greater than the maximum size of particles able to pass through respective ones of said filter elements located further from said distal end of said flexible elongate member.

25. The device of claim 21 wherein said stocking is of a filter medium substantially preventing passage of particles which are larger than a predetermined size.

26. The device of claim 21 wherein said means for selectively closing said mouth includes a drawstring attached to said stocking and extending along said elongate flexible support member toward said distal end thereof.

27. The device of claim 21 including a plurality of drawstrings arranged for coordinated application of tension thereto for drawing said stocking and said filter elements into a furled configuration.

28. The device of claim 21 wherein said elongate flexible support member is a guide wire and includes a flexible tip portion extending distally beyond all of said filter elements.

29. The device of claim 28 wherein said guide wire has a reduced diameter portion to which said filter elements are attached, said tip portion being larger in diameter than reduced diameter portion.

30. The device of claim 21 including a set of flexible resilient ribs extending radially from said flexible elongate support member adjacent one of said filter elements so as to urge said filter element toward a radially extended configuration.

31. A method of relieving a stenosis in a blood vessel, comprising the steps of:

(a) providing an endovascular filter device, including a slender flexible elongate support member having a proximal end and a distal end adapted for insertion into and along the interior of a blood vessel and a flexible tubular porous stocking surrounding a portion of said elongate support member, the stocking having a mouth directed generally toward said distal end of said elongated member, as well as a closed end surrounding said elongate member and located more proximally along said elongate member than the location of said mouth, and means for supporting said tubular stocking with said mouth open to receive a flow of blood;

(b) forming an opening in a blood vessel in a location downstream of a stenotic portion thereof by reference to the normal flow of blood, and inserting said flexible elongate support member into said blood vessel through said opening, with said stocking in a furled configuration;

(c) extending said filter device into said blood vessel until said stocking has approached to within a predetermined distance from said stenotic portion on a downstream side of said stenotic portion of said blood vessel;

(d) thereafter unfurling said stocking so as to deploy said stocking within said blood vessel with said mouth of said stocking substantially in intimate contact with the interior of said blood vessel;

(e) thereafter enlarging the lumen of said blood vessel by freeing pieces of material from said stenotic portion thereof;

(f) entrapping within said stocking said pieces of material thus freed from said stenotic portion; and (g) reducing the diameter of said stocking to a reduced diameter by twisting said stocking about said flexible elongate support member prior to removing said filter from said blood vessel.

32. A method of relieving a stenosis in a blood vessel, comprising the steps of:

(a) providing an endovascular filter device, including a slender flexible elongate support member having a proximal end and a distal end adapted for insertion into and along the interior of a blood vessel and a flexible tubular porous stocking surrounding a portion of said elongate support member, said tubular porous stocking having an interior and including a plurality of flexible filter elements attached to said elongate support member and spaced apart from one another therealong within said flexible tubular porous stocking, each of said filter elements being interconnected with the interior of said tubular porous stocking, the stocking having a mouth directed generally toward said distal end of said elongate member, as well as a closed end surrounding said elongate member and located more proximally along said elongate member than the location of said mouth, and means for supporting said tubular stocking with said mouth open to receive a flow of blood;

(b) forming an opening in a blood vessel in a location downstream of a stenotic portion thereof by reference to the normal flow of blood, and inserting said flexible elongate support member into said blood vessel through said opening, with said stocking in a furled configuration;

(c) extending said filter device into said blood vessel until said stocking has approached to within a predetermined distance from said stenotic portion on a downstream side of said stenotic portion of said blood vessel;

(d) thereafter unfurling said stocking so as to deploy said stocking within said blood vessel with said mouth of said stocking substantially in intimate contact with the interior of said blood vessel;

(e) thereafter enlarging the lumen of said blood vessel by freeing pieces of material from said stenotic portion thereof; and (f) entrapping within said stocking said pieces of material thus freed from said stenotic portion.

33. An endovascular filter device, comprising:

(a) a slender flexible elongate support member having a proximal end and a distal end adapted for insertion into and along the interior of a blood vessel; and (b) a filter assembly including:
  (i) a flexible tubular porous stocking surrounding a portion of said elongate support member proximate said distal end and having a closed end attached to said elongate support member and a mouth directed generally toward said proximal end of said elongate support member;
  (ii) means for supporting said tubular porous stocking with said mouth open to receive a flow of blood in a flow-receiving and filtering position within said blood vessel; and
  (iii) selectively operable means associated with said mouth for closing said mouth about said elongate support member and twisting said stocking about said elongate support member to retain materials filtered from said flow of blood within said stocking, said selectively operable means including a drawstring interconnecting said elongate support member and said mouth, and means extending through said elongate support member for controlling said drawstring in order to close said mouth and twist said stocking about said elongate support member.

* * * * *